US00PP29708P2

(12) United States Plant Patent
Arts

(10) Patent No.: US PP29,708 P2
(45) Date of Patent: Sep. 25, 2018

(54) ***MANDEVILLA* PLANT NAMED 'MAN217901'**

(50) Latin Name: *Mandevilla sanderi*
Varietal Denomination: MAN217901

(71) Applicant: Niels Arts, Aalsmeer (NL)

(72) Inventor: Niels Arts, Aalsmeer (NL)

(73) Assignee: MBA B.V., DeKwakel (NL)

( * ) Notice: Subject to any disclaimer, the term of this patent is extended or adjusted under 35 U.S.C. 154(b) by 0 days.

(21) Appl. No.: 15/731,680

(22) Filed: Jul. 15, 2017

(51) Int. Cl.
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. A. Whealy

(57) ABSTRACT

A new and distinct cultivar of *Mandevilla* plant named 'MAN217901', characterized by its upright and spreading plant habit; vigorous growth habit; freely branching habit; relatively small glossy green-colored leaves; early and freely flowering habit; and large flowers with broad red purple-colored petals.

2 Drawing Sheets

Botanical designation: *Mandevilla sanderi*.
Cultivar denomination: 'MAN217901'.

BACKGROUND OF THE INVENTION

The present invention relates to a new and distinct cultivar of *Mandevilla* plant, botanically known as *Mandevilla sanderi* and hereinafter referred to by the name 'MAN217901'.

The new *Mandevilla* plant is a product of a planned breeding program conducted by the Inventor in De Kwakel, The Netherlands. The objective of the breeding program is to create new freely-flowering *Mandevilla* plants with large and attractive flowers.

The new *Mandevilla* plant originated from an open-pollination in De Kwakel, The Netherlands in May, 2012 of a proprietary selection of *Mandevilla sanderi* identified as code number 11-0006-000, not patented, as the female, or seed parent with an unknown selection of *Mandevilla sanderi* as the male, or pollen, parent. The new *Mandevilla* plant was discovered and selected by the Inventor as a single flowering plant from within the progeny of the stated open-pollination in a controlled greenhouse environment in De Kwakel, The Netherlands in May, 2014.

Asexual reproduction of the new *Mandevilla* plant by vegetative cuttings in a controlled greenhouse environment in De Kwakel, The Netherlands, since August, 2014 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN217901'. These characteristics in combination distinguish 'MAN217901' as a new and distinct *Mandevilla* plant:

1. Upright and spreading plant habit.
2. Vigorous growth habit.
3. Freely branching habit.
4. Relatively small glossy green-colored leaves.
5. Early and freely flowering habit.
6. Large flowers with broad red purple-colored petals.

Plants of the new *Mandevilla* can be compared to plants of the female parent selection. Plants of the new *Mandevilla* differ primarily from plants of the female parent selection in flower color as plants of the female parent selection have white-colored flowers.

Plants of the new *Mandevilla* can be compared to plants of *Mandevilla hybrida* 'Sunparapibra', disclosed in U.S. Plant Pat. No. 19,649. In side-by-side comparisons, plants of the new *Mandevilla* differ primarily from plants 'Sunparapibra' in the following characteristics:

1. Plants of the new *Mandevilla* are more vigorous than plants of 'Sunparapibra'.
2. Plants of the new *Mandevilla* are more freely branching than plants of 'Sunparapibra'.
3. Plants of the new *Mandevilla* flower earlier than plants of 'Sunparapibra'.
4. Plants of the new *Mandevilla* are more freely flowering than plants of 'Sunparapibra'.
5. Plants of the new *Mandevilla* have larger flowers than plants of 'Sunparapibra'.
6. Petals of plants of the new *Mandevilla* are darker red purple in color than petals of plants of 'Sunparapibra'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet is a side perspective view of typical flowering plant of 'MAN217901' grown in a container.

The photograph on the second sheet is close-up view of a typical flowering plant of 'MAN217901'.

DETAILED BOTANICAL DESCRIPTION

The aforementioned photographs and following observations, measurements and values describe plants grown during the late spring in 19-cm containers in a glass-covered greenhouse in De Kwakel, The Netherlands and under cultural practices typical of *Mandevilla* commercial production. During the production of the plants, day temperatures ranged from 20° C. to 22° C. and night temperatures averaged 18° C. Plants were pinched one time four weeks after planting. Plants were twelve months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'MAN217901'.

Parentage:

*Female, or seed, parent*.—Proprietary selection of *Mandevilla sanderi* identified as code number 11-0006-000, not patented.

*Male, or pollen, parent*.—Unknown selection of *Mandevilla sanderi*, not patented.

Propagation:

*Type*.—By vegetative cuttings.

*Time to initiate roots, summer*.—About 21 days at temperatures about 22° C.

*Time to initiate roots, winter*.—About 27 days at temperatures about 22° C.

*Time to produce a rooted young plant, summer*.—About 40 days at temperatures about 22° C.

*Time to produce a rooted young plant, winter*.—About 50 days at temperatures about 22° C.

*Root description*.—Medium in thickness, fibrous to slightly fleshy; typically whitish brown in color, actual color of the roots is dependent on substrate composition, water quality, fertilizers, substrate temperature and physiological age of roots.

*Rooting habit*.—Freely branching; medium density.

Plant description:

*Plant and growth habit*.—Upright and spreading plant habit; short internodes, dense and bushy appearance; vigorous growth habit; rapid growth rate.

*Plant height, soil level to top of foliar plane*.—About 66 cm.

*Plant height, soil level to top of floral plane*.—About 66 cm.

*Plant diameter* (*spread*).—About 50 cm.

*Lateral branch description*.—Branching habit: Freely branching habit with about four primary branches, each with about three to five secondary lateral branches. Length, primary branches: About 30 cm to 40 cm. Length, secondary branches: About 5 cm to 15 cm. Diameter, primary and secondary branches: About 4 mm. Internode length: About 2 cm to 5 cm. Strength: Strong. Texture and luster: Smooth, glabrous; semi-glossy becoming woody and matte with development. Color, developing: Close to 144A. Color, developed: Close to 152B; when woody, close to N199C.

Leaf description:

*Arrangement*.—Opposite, simple; relatively small.

*Length, fully expanded leaves*.—About 5 cm to 7 cm.

*Width, fully expanded leaves*.—About 3.5 cm.

*Shape*.—Ovate.

*Apex*.—Cuspidate.

*Base*.—Obtuse.

*Margin*.—Entire.

*Texture and luster, upper and lower surfaces*.—Smooth, glabrous; leathery; glossy.

*Venation pattern*.—Pinnate.

*Color*.—Developing leaves, upper surface: Close to 146A. Developing leaves, lower surface: Close to 146C. Full expanded leaves, upper surface: Close to 147A; main vein, close to 143C and lateral venation, close to 147A. Fully expanded leaves, lower surface: Close to 146B; main vein, close to 145B and lateral venation, close to 146B.

*Petioles*.—Length: About 1 cm to 1.5 cm. Diameter: About 2 mm. Strength: Strong. Texture and luster, upper and lower surfaces: Smooth, glabrous; semi-glossy. Color, upper and lower surfaces: Close to 144B.

Flower description:

*Flower type and flowering habit*.—Single salverform flowers arranged in axillary racemes; flowers star-shaped and face upright to outwardly; freely flowering habit with about seven to eight flowers per inflorescence and during the flowering season, about 25 open flowers and about 100 flower buds per plant.

*Natural flowering season*.—Plants flower continuously from late spring until frost in the autumn in The Netherlands; early flowering habit, plants begin flowering about seven months after planting.

*Flower longevity on the plant*.—About eight to ten days; flowers not persistent.

*Fragrance*.—Slightly fragrant, pleasant.

*Inflorescence height*.—About 10 cm to 15 cm.

*Inflorescence diameter*.—About 10 cm to 15 cm.

*Flower buds*.—Length: About 7.5 cm. Diameter: About 1.2 cm. Shape: Elongated, spindle-shaped. Texture and luster: Smooth, glabrous; semi-glossy. Color: Close to 145B; towards the base, close to 63B.

*Flowers*.—Appearance: Flared trumpet, corolla fused and five-parted. Diameter: About 8 cm to 9 cm. Length: About 7 cm. Throat diameter: About 1.5 cm. Tube length: About 4 cm to 5 cm. Tube diameter, proximally: About 4 mm.

*Corolla*.—Quantity and arrangement: Five petals arranged in a single whorl; proximal portion of the petals are fused into a tube; distal free portions slightly imbricate. Petal length: About 3.5 cm to 4 cm. Petal width: About 2.5 cm to 3 cm. Petal shape and appearance: Ovate to triangular, asymmetrical. Petal apex: Acute. Petal margin: Entire; slightly undulate. Petal texture and luster, upper and lower surfaces: Smooth, glabrous; semi-glossy. Throat and tube texture: Smooth, glabrous. Color: Petal, when opening, upper surface: Close to N57B. Petal, when opening, lower surface: Close to N57B; towards the base, close to 145D. Petal, fully opened, upper surface: Close to N57A; towards the throat, close to 53C; venation, close to 53C; color does not change with development. Petal, fully opened, lower surface: Close to 58B; venation, close to N57B; color does not change with development. Throat: Close to N25B; venation, close to 62C and 53C. Tube: Close to 58B; towards the base, close to 145C; venation, similar to ground colors.

*Calyx*.—Quantity and arrangement: Five sepals arranged in a single whorl; calyx, star-shaped. Length: About 5 mm to 8 mm. Diameter: About 6 mm. Sepal length: About 6 mm to 7 mm. Sepal width: About 2 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 144C; towards the apex, close to 181B. Fully opened, upper and lower surfaces: Close to 144C; towards the apex, close to 181B.

*Peduncles*.—Length: About 2.5 cm. Diameter: About 2 mm to 3 mm. Strength: Strong. Aspect: Mostly upright. Texture and luster: Smooth, glabrous; glossy. Color: Close to 144A.

*Pedicels*.—Length: About 2 cm. Diameter: About 2 mm. Strength: Strong. Aspect: Upright to about 30° from peduncle axis. Texture and luster: Smooth, glabrous; glossy. Color: Close to 144A.

*Reproductive organs*.—Stamens: Quantity and arrangement: Typically five; basifixed; anthers connivent. Filament color: Close to 14D. Anther length: About 8 mm. Anther shape: Elliptic. Anther color: Close to 18A. Pollen amount: Moderate. Pollen color: Close to 155D. Pistils: Quantity: Typically one. Pistil length: About 2.5 cm. Style color: Close to 145C. Stigma diameter: About 2 mm. Stigma shape: Club-shaped. Stigma color: Close to 144C. Ovary color: Close to 144B.

*Fruits and seeds*.—Fruit and seed development have not been observed on plants of the new *Mandevilla* to date.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate temperatures ranging from about 1° C. to about 45° C.

It is claimed:

1. A new and distinct *Mandevilla* plant named 'MAN217901' as illustrated and described.

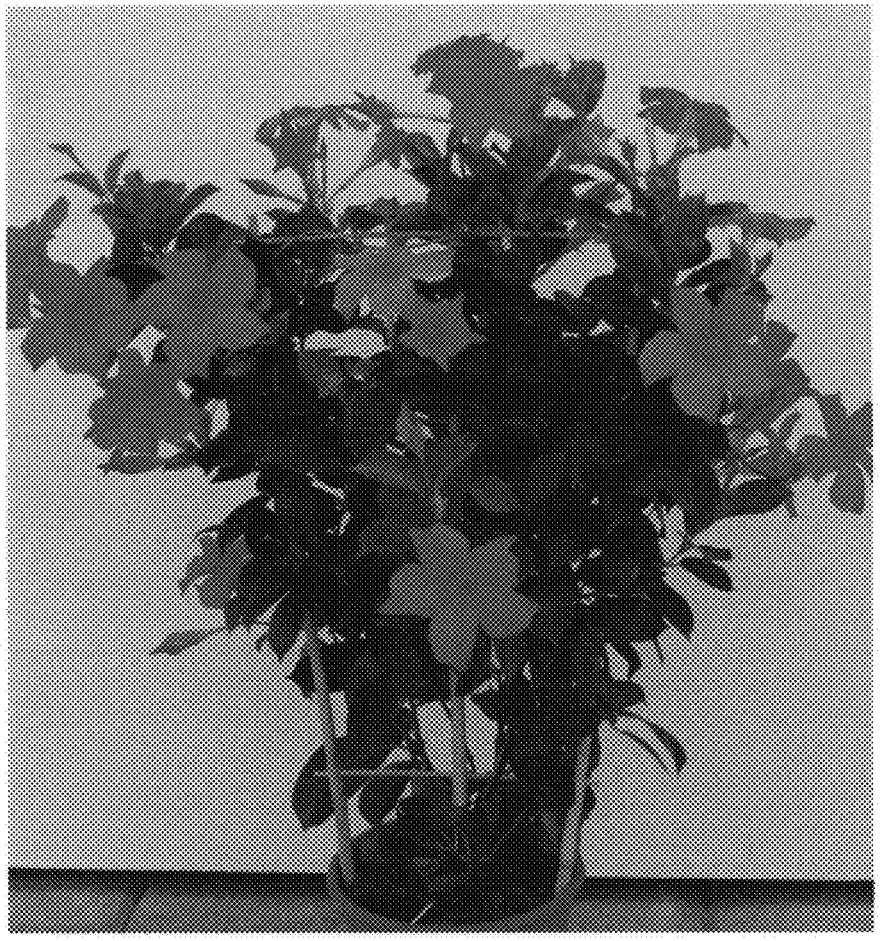

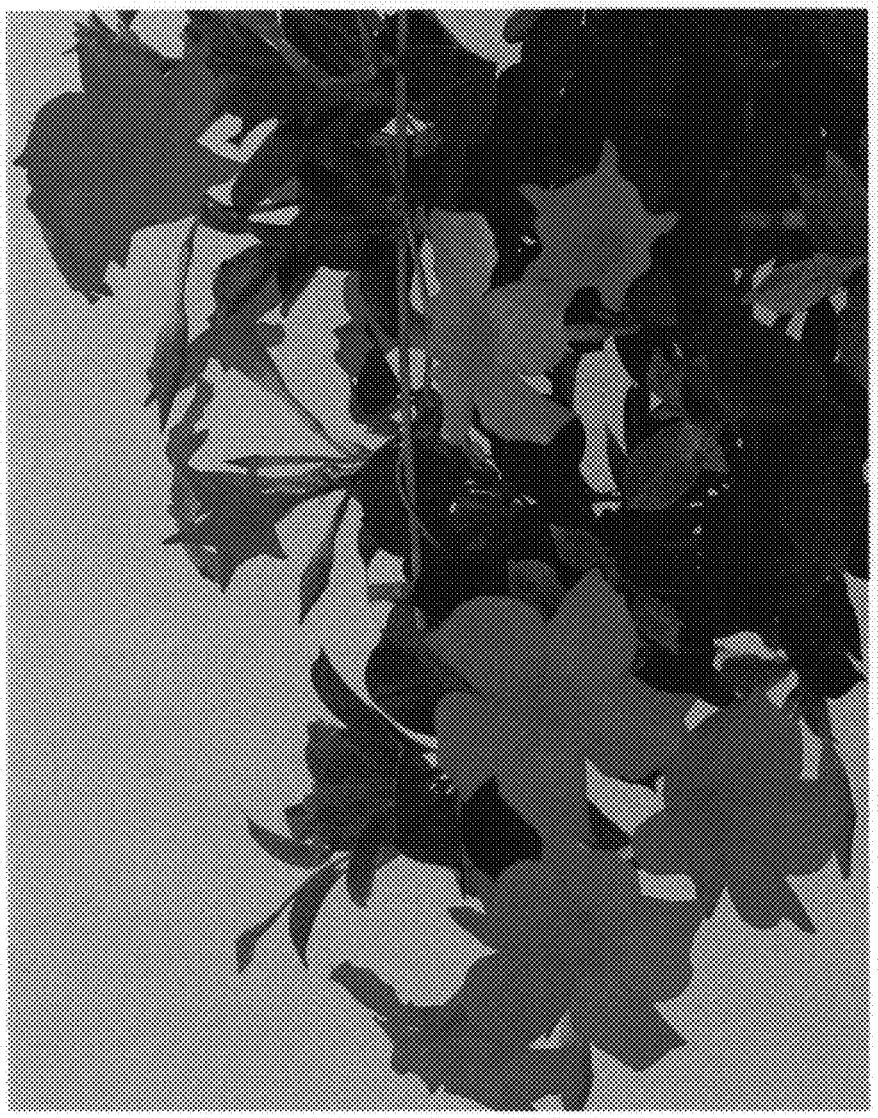

* * * * *